United States Patent [19]

Papp et al.

[11] 4,312,837
[45] Jan. 26, 1982

[54] HYDROFORMYLATION LOOP REACTORS

[75] Inventors: Roger Papp, Paris; Francois Mongenet, Saint Symphorien D'Ozon, both of France

[73] Assignee: Produits Chimiques Ugine-Kuhlmann, Courbevoie, France

[21] Appl. No.: 196,489

[22] PCT Filed: Jul. 13, 1979

[86] PCT No.: PCT/FR79/00065
§ 371 Date: Mar. 13, 1980
§ 102(e) Date: Mar. 13, 1980

[30] Foreign Application Priority Data
Jul. 13, 1978 [FR] France ............................... 78 20970

[51] Int. Cl.³ .................... B01J 4/00; B01J 14/00; B01J 19/24
[52] U.S. Cl. .................................. 422/224; 422/235
[58] Field of Search .............. 422/214, 215, 224, 230, 422/235; 568/451

[56] References Cited
U.S. PATENT DOCUMENTS

| | | | |
|---|---|---|---|
| 3,188,351 | 6/1965 | Lemke | 568/456 |
| 3,458,467 | 7/1969 | Herrle et al. | 260/29.6 |
| 3,859,367 | 1/1975 | Yamamoto et al. | 260/633 |
| 3,957,442 | 5/1976 | Yamamoto et al. | 422/224 |

Primary Examiner—Bradley Garris
Attorney, Agent, or Firm—Sigalos & Levine

[57] ABSTRACT

This invention relates to improved hydroformylation reactors of the "loop" type comprising two parallel vertical tubes, one of said tubes having a supply tube at its base and acting as the ascending branch and the other of said tubes acting as the descending branch, and means connecting said tubes to one another at their top and bottom ends, the improvement comprising a tubular loop connecting said tubes at their upper ends, and an evacuation orifice for synthesis gases and excess liquid phase from said tubular loop, said orifice having a smaller diameter than the internal diameter of said tubular loop.

9 Claims, 12 Drawing Figures

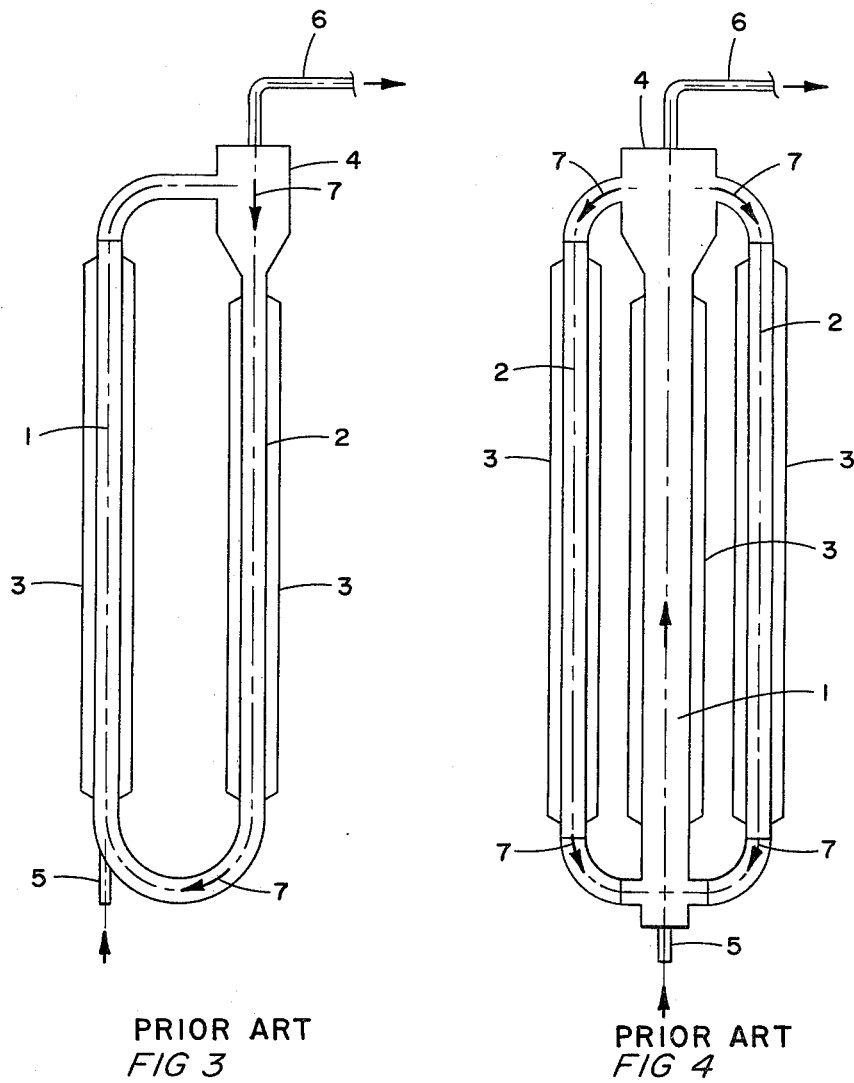
PRIOR ART
FIG 3
PRIOR ART
FIG 4
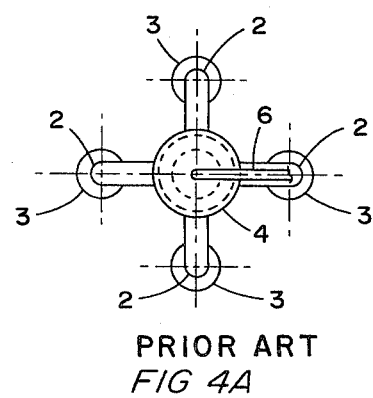
PRIOR ART
FIG 4A

HYDROFORMYLATION LOOP REACTORS

BACKGROUND OF THE INVENTION

This invention relates to an improvement to reactors intended for hydroformylation. The hydroformylation reaction, also known as Oxo synthesis, consists in reacting a synthesis gas made up of a mixture of carbon monoxide and hydrogen with an olefin containing "n" carbon atoms so as to obtain a mixture of aldehydes and primary alcohols containing n+1 carbon atoms. The reaction is generally catalysed with carbonyls of transition metals, more particularly cobalt hydrocarbonyl or dicobalt octocarbonyl. This type of reaction is described in U.S. Pat. No. 3,188,351.

The reactor generally used for this type of continuous reaction is of the "loop" type in which the liquid phase is recycled according to the gas pump principle. This reactor is made up of at least two parallel vertical tubes connected to each other at their upper and lower ends. At least one of the vertical tubes acts as the ascending branch and is continuously supplied at its base with the synthesis gas and liquid phase while at least one vertical tube acting as the descending branch allows only the liquid phase to circulate, and all the synthesis gas and the excess liquid phase are evacuated at the upper connection. To achieve this, the reactor comprises, at its top, a broad bell-mouth which makes it easier to separate all the synthesis gases from the liquid phase which is to be recycled. The difference between the specific gravities of the gas/liquid phase mixture on the one hand and the liquid phase alone on the other hand results in a difference in hydrostatic pressure between the ascending branch and the descending branch, thus leading to circulation of the liquid phase in the reactor.

These types of reactors are entirely satisfactory with regard to the circulation of the liquid phase, but have serious drawbacks with regard to the hydroformylation catalyst. The transition metal carbonyls used as catalysts are known to be unstable products which tend to decompose thereby producing a metal compound and giving off carbon monoxide. This is why Oxo synthesis is carried out under pressure as the carbonyls are all the more stable as the partial pressure of carbon monoxide is higher. In the reactors described above, the liquid phase, which also contains catalyst, circulating in the descending branch is totally free of any free synthesis gas and is subject to conditions in which the carbonyls are very unstable thus leading to the decomposition and depositing of metal compounds on the walls of the descending branch. This eventually leads to plugging this branch. Moreover, the productivity of the reactors is reduced owing to the lack of reactive synthesis gases in the descending branch.

It has been found that, by modifying the geometry of the upper connection of the vertical tubes, it is possible not only to eliminate the above-mentioned disadvantages relating to the catalyst, but also to increase the productivity of the reactors considerably. This improvement, the purpose of which is to allow synthesis gas to be entrained into the descending branch where, according to the prior art, only the gas-free liquid phase circulates, is characterised in that the upper connection of the vertical tubes is a tubular loop with an evacuation orifice for the synthesis gases and excess liquid phase, the diameter of which is less than the internal diameter of the said connection or tubular loop. This constriction at the point of evacuation of the gases creates a sort of flooding or obstruction which causes entraining of the synthesis gases such that the liquid phase in the descending branch is always saturated with gas. As an indication, it is estimated that the fraction, by volume, of gas entrained represents between 0.2 and 1% of the volume of liquid in the descending branch.

SUMMARY OF THE INVENTION

Thus, the present invention is an improvement in hydroformylation reactors of the "loop" type comprising of two parallel vertical tubes, one of said tubes having a supply tube at its base and acting as the ascending branch and the other of said tubes acting as the descending branch and means connecting said tubes to each other at their top and bottom ends, the improvement comprising a tubular loop connecting said vertical tubes at their upper ends and an evacuation orifice for synthesis gases and excess liquid phase from said tubular loop, said orifice having a smaller diameter than the internal diameter of said tubular loop.

BRIEF DESCRIPTION OF THE DRAWINGS

These and other objects and advantages of the present invention will be disclosed in the course of the following specification, reference being made to the accompanying drawings in which:

FIGS. 1 through 4 are side views of prior art hydroformylation reactors of the "loop" type conventionally used;

FIG. 4A is a top view of the reactor of FIG. 4;

DETAILED DESCRIPTION OF THE PREFERRED EMBODIMENT

Figure 1:
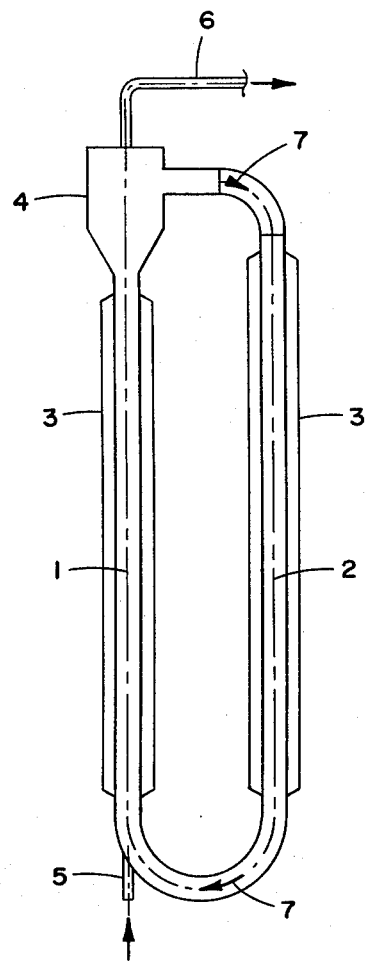
Figure 2:
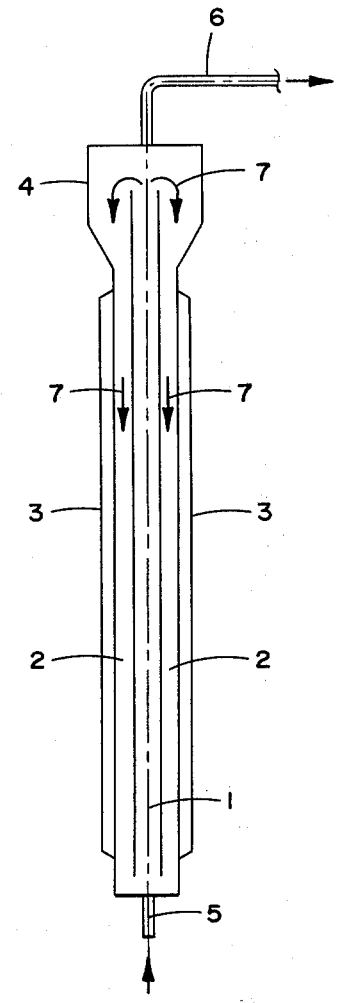
Figure 5:
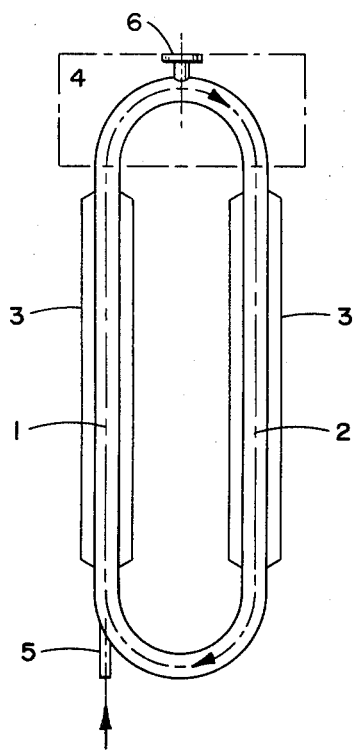
FIGS. 5 through 8 are side views and partial side views of a hydroformylation reactor of the present invention in which a tubular loop of semi-toric shape connects the vertical tubes of the reactor at their top.
Figure 8:
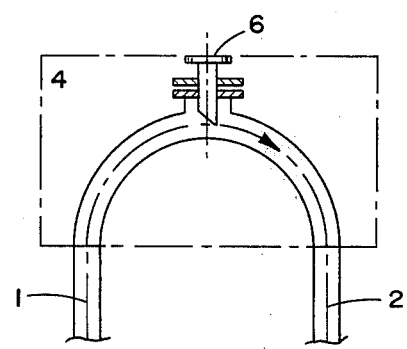
Figure 9:
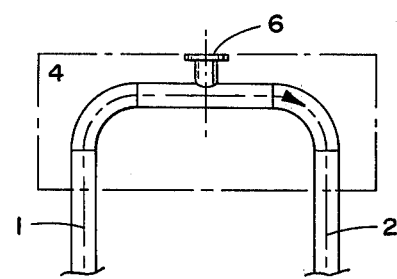
FIGS. 9 through 11 are partial side views of a hydroformylation reactor of the present invention in which a tubular loop of roughly rectangular shape connects the vertical tubes of the reactor at their top.

To make the improvement according to the invention easier to understand, FIGS. 1 to 4 show the reactors conventionally used and their method of operation. In the ascending branch 1, supplied via nozzle 5 with a mixture of synthesis gases and liquid phase, there circulate the reagents which separate in the bell-mouth 4, all the synthesis gases and the excess liquid phase being evacuated via nozzle 6, whereas the liquid phase 7, free of synthesis gases, circulates in the descending branch 2. The vertical tubes are provided with cooling means 3.

The reactor according to the present invention is also a "loop" type reactor consisting of two parallel vertical tubes connected in known manner at their lower parts. Again, one of the tubes, supplied at its base with synthesis gases and liquid phase, serves as the ascending branch and one of the tubes serves as the descending branch. However, these vertical tubes are connected to each other at their upper portion by a tubular loop the internal diameter of which may be between d/2 and 2 d, preferably between 0.8 d and 1.2 d, for an internal diameter "d" of the ascending branch. The term "tubular loop" refers to any connection between said parallel vertical tubes including two 90° elbows, and at the utmost making a semi-torus, the bending radius of said elbows, measured at their axis being preferably between 1.5 d and 5 d, and usually between 2 d and 3 d.

The tubular loop is provided with an evacuation orifice, preferably substantially along the vertical axis of the reactor. This evacuation orifice for the synthesis gases and excess liquid phase has a diameter, in relation to the diameter "d" of the ascending branch, which is usually less than d/2 and greater than d/10, preferably between d/3 and d/7. In practice, the evacuation orifice may consist of an extraction nozzle having an internal diameter as defined above and fixed to the tubular loop.

Figure 6:
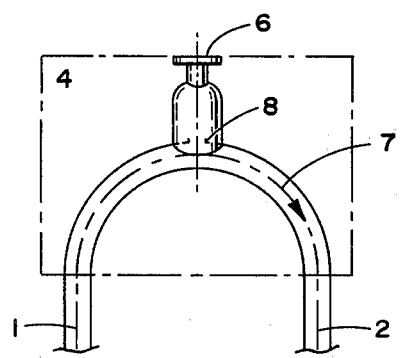
Figure 10:
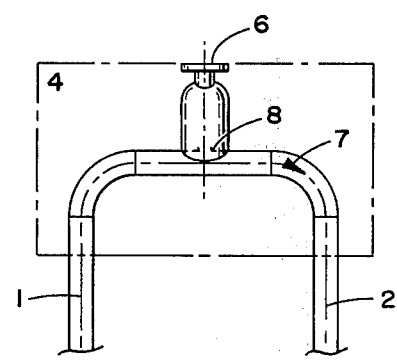

FIGS. 5 to 11 show different types of reactors according to the invention, without being restrictive. In these Figures, 1 and 2 represent, respectively, the ascending and descending branches, 3 the cooling means, 4 the upper, connecting tubular loop, 5 the supply tube for synthesis gases and liquid phase, and 6 the extraction nozzle. FIGS. 6 and 10 show an alternative embodiment in which the extraction of the synthesis gases and excess liquid phase is effected through an evacuation orifice 8 placed as close as possible to the line of tangency of the tubular loop. In this case, the evacuation orifice 8 has an internal diameter, based on the diameter "d" mentioned above, which is generally less than d/2 and greater than d/10, preferably between d/3 and d/7; consequently the extraction nozzle 6 may have any desired diameter, provided always that it is equal to or greater than that of the evacuation orifice 8.

The extraction nozzles are fixed to the tubular loop by any known means, such as, for example, by welding or by a leaktight connection.

The advantages of this improvement to hydroformylation reactors include: the absence of metal deposits in the descending branch, the increased productivity, the speed of recycling of the liquid phase which is comparable to that obtained in conventional reactors, and the quality of the recycling of the liquid.

The entraining of the synthesis gases into the descending branch ensures perfect stability of the metal carbonyls used as catalysts. There are virtually no metal deposits on the walls of the descending branch. Owing to the improvement obtained according to the invention, the duration of the cycles between two cleanings of the reactor is from 24 to 36 months, instead of 1 to 3 months for an equivalent reactor according to the prior art.

The fact that synthesis gas is present in the descending branch means that the productivity of the reactors can be improved by up to 20%, all other conditions being unchanged. According to the prior art, only that part of the synthesis gas dissolved in the liquid phase can react in the descending branch. Moreover, in the prior art, since the synthesis gas has been extracted, there is no longer a sufficient quantity of synthesis gas present in the lower part of the descending branch, resulting not only in the decomposition of the catalyst but also in stoppage of the reaction owing to lack of reagent. In the present invention, on the other hand, thanks to the entraining of synthesis gas into the descending branch, there is always enough reagent to enable the hydroformylation reaction to continue and the catalyst is not decomposed.

Figure 7:
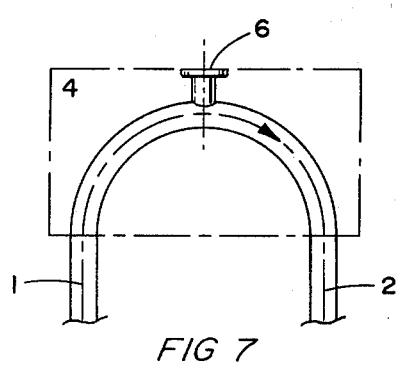
Figure 11:
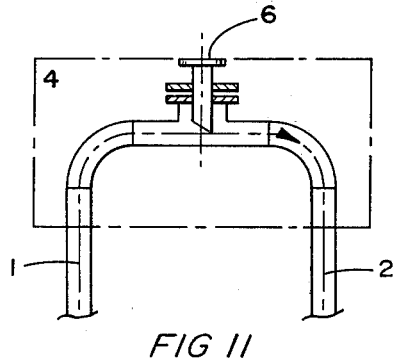

Surprisingly, in this "loop" type reactor, the entraining of synthesis gas into the descending branch has almost no effect on the speed of recycling of the liquid. Thus, in a reactor consisting of 2 vertical tubes with an internal diameter of 273 mm and a height of 40 meters, the speeds of recycling of the liquid were measured by radioactive tracing. For a prior art reactor of the kind shown in FIG. 3, the speeds of recycling of the liquid are between 1.0 and 1.6 m/second according to the flow rate of the synthesis gas under industrial operating conditions. With the present invention, for the same reactor modified in its upper part by the novel tubular loop as shown in FIG. 7, wherein the extraction nozzle, having an internal diameter of 89 mm, is placed on a toric junction with an internal diameter of 300 mm, and with a radius of curvature of 750 mm, the speeds of recycling of the liquid, under the same industrial operating conditions, are between 1.0 and 1.5 m/second. This maintenance of a high recycling speed also promotes the mixing of the synthesis gas and the liquid phase.

The quality of recycling in the improved reactors can be checked by the absence of any significant temperature differences between two points of the reactor and any measurable differences in concentration of the liquid phase inside the reactor.

The following example illustrates, by comparison, the advantages of the improvement with an industrial unit:

EXAMPLE

In a series of 3 reactors, each consisting of 2 vertical tubes with an internal diameter of 317.5 mm and a height of 40 meters, the internal diameter of the upper elbow bends is 300 mm, the radius of curvature of the same bends measured at the axis of the bend is 750 mm and the extraction nozzles, placed vertically on the axis of the reactors, have an internal diameter of 89 mm.

When this series of reactors is used for the production of isodecyl alcohol from a propylene trimer and synthesis gas, the total flow rate of synthesis gas fed into the first reactor is 2,750 standard m$^3$/hr, 350 standard m$^3$/hr of which are recycled, whilst 2,400 standard m$^3$/hr consist of new gas. The flow rate of gas consumed by the reaction represents about 1,900 standard m$^3$/hr.

Taking into account the consumption of synthesis gas in each of the reactors, the speeds of the gas in the upper elbow bends, measured at 0° C. and at atmospheric pressure, are:
approximately 5.6 m/sec at the first reactor
approximately 3.2 m/sec at the last reactor.

The duration of the cycle between two cleaning operations is 24 months, on the average, and the production capacity of this reaction line is up to 160 T/day of alcohol.

For the same line of reactors fitted with an upper connection in the form of a bell-mouth according to FIG. 3, with all other conditions being equal, the duration of the cycle between two cleaning operations is only 3 months, on the average, and the production capacity is only 130 T/day of alcohol.

While the invention has been described in connection with a preferred embodiment, it is not intended to limit the scope of the invention to the particular form set forth, but, on the contrary, is intended to cover such alternatives, modifications, and equivalents as may be included within the spirit and scope of the invention as defined by the appended claims.

What is claimed is:

1. In a hydroformylation reactor of the "loop" type comprising two parallel vertical tubes, one of said tubes having a supply tube at its base and acting as the ascending branch and the other of said tubes acting as the descending branch, and means connecting said vertical tubes to each other at their top and bottom ends, the improvement comprising:
 a. A tubular loop connecting said vertical tubes at their upper ends, and
 b. outlet means consisting of an evacuation orifice for removing synthesis gases and excess liquid phase from said tubular loop located along the vertical axis of said reactor, said orifice having a smaller diameter than the internal diameter of said tubular loop.

2. In a hydroformylation reactor of the "loop" type comprising two parallel vertical tubes, one of said tubes having a supply tube at its base and acting as the ascending branch and the other of said tubes acting as the descending branch, and means connecting said vertical tubes to each other at their top and bottom ends, the improvement comprising:
 a. a tubular loop connecting said vertical tubes at their upper ends, and
 b. outlet means consisting of an evacuation orifice for removing synthesis gases and excess liquid phase from said tubular loop, said orifice containing a constriction at the point of evacuation thereby creating an obstruction which causes entraining of said synthesis gases such that said liquid phase in said descending branch is always saturated with said synthesis gas.

3. A reactor as in claims 1 or 2 further comprising:
 a. an ascending branch having an internal diameter, d,
 b. a tubular loop of internal diameter between d/2 and 2 d, and
 c. an evacuation orifice having an internal diameter of less than d/2 and greater than d/10.

4. A reactor as in claim 3 wherein said evacuation orifice is located as close as possible to the line of tangency of said tubular loop.

5. A reactor as in claim 4 wherein said evacuation orifice comprises an extraction nozzle fixed to said tubular loop.

6. A reactor as in claim 5 wherein said tubular loop has a radius of curvature of between 1.5 d and 5 d.

7. A reactor as in claim 6 wherein said tubular loop is semi-toric in shape.

8. A reactor as in claim 7 wherein said tubular connecting loop is roughly rectangular in shape.

9. A reactor as in claim 2 wherein said evacuation orifice is located along the vertical axis of said reactor.

* * * * *